United States Patent [19]

Ono

[11] Patent Number: 5,163,442
[45] Date of Patent: Nov. 17, 1992

[54] FINGER TIP BLOOD COLLECTOR

[76] Inventor: Harry Ono, 1890 Big Ben Dr., Des Plaines, Ill. 60061

[21] Appl. No.: 738,159

[22] Filed: Jul. 30, 1991

[51] Int. Cl.⁵ ................................................. A61B 5/14
[52] U.S. Cl. ................................... 128/760; 128/762; 128/767; 128/770
[58] Field of Search ................ 128/760, 762, 767, 770, 128/637–638; 604/322, 415, 355, 3; 606/181–182

[56] References Cited

U.S. PATENT DOCUMENTS

| | | | |
|---|---|---|---|
| 2,025,492 | 11/1934 | Aird | 604/355 |
| 3,954,105 | 5/1976 | Nordby et al. | 604/355 |
| 4,250,882 | 2/1981 | Adair | 604/355 |
| 4,468,227 | 8/1984 | Jensen | 128/760 |

Primary Examiner—William E. Kamm
Assistant Examiner—J. R. Jastrzab
Attorney, Agent, or Firm—Hill, Van Santen, Steadman & Simpson

[57] ABSTRACT

A blood collector comprises a thin flexible tube, which adheres to a person's finger, and the finger is punctured through the tube. The outside surface of the tube is sealed after the puncture, and a quantity of blood from the finger is collected in the tube.

16 Claims, 6 Drawing Sheets

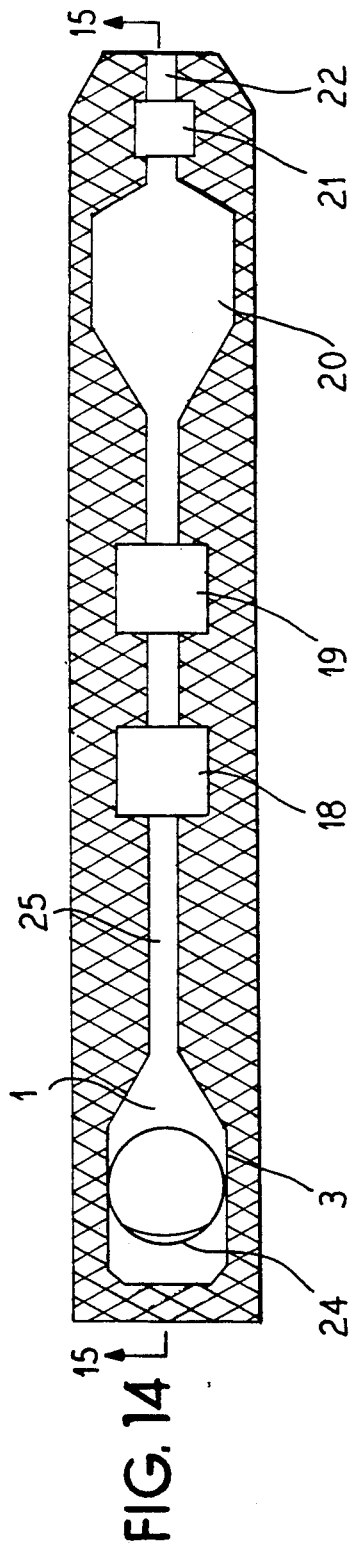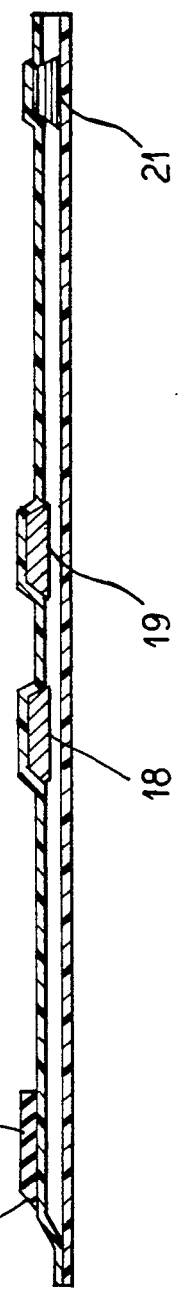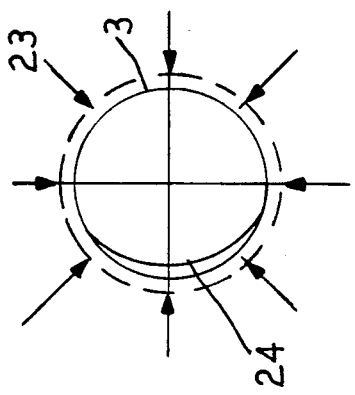

FINGER TIP BLOOD COLLECTOR

BACKGROUND

This invention relates to an appliance to be used for collecting a sample of blood accumulated through a skin puncture on the finger tip or heel of a patient and designed with a sealed chamber to receive the flow of blood without exposure to the environment.

The current method of obtaining a small sample of blood for processing is by lancing a finger tip or heel and squeezing out a drop or two of blood, which is then wetted onto a reagent test strip, placed on a glass slide or collected into a small capillary tube. The blood flows out onto the patient's skin without restriction and quite often drips and splatters, especially in the case of small children or disoriented persons who cannot keep still. This creates an inconvenience and increases the risk of contamination to the nurse or doctor.

If a test is done at the bedside, for example for glucose, the blood is smeared onto a test strip and processed by a set procedure, then recorded. It is much easier and expedient for the attendant to collect all the samples and then process them at one location such as the nurse's station or desk. A sealed collector provides a convenient means for this procedure.

After collecting or processing the sample, the patient's finger (or heel) is wiped clean then sometimes bandaged with a band aid, or the like.

SUMMARY OF THE INVENTION

It is desirable to provide a blood collector which avoids the disadvantages of the current method and which offers a simple and effective blood collector. This invention contains an adhesive section which remains on the patient, which eliminates the need for cleaning and application of a bandage.

There are several variations of this invention. One configuration is a blood collector only. Another embodiment contains a reagent or a number of reagents for the purpose of performing the necessary tests completely within the collector. Another embodiment contains an extra large chamber for collecting larger amounts of blood.

A further embodiment incorporates a tapered connector for the attachment of various items, such as reagents, capillary tubes, coagulators, or the like.

Since the blood flow through a standard lanced hole is quite small, this invention also includes a means to obtain a large amount of blood without using multiple punctures or the larger scalpel type lancet.

The adhesive seal between the container and the skin must be reliable and tenacious; therefore the adhesive patch design and a method of application are also included in this invention.

The appliance of the present invention is a low cost, disposable plastic tube and sleeve which is placed onto the finger or heel and designed for the collection of blood that flows out of a lanced puncture, accumulated directly into a closed tube. After the desired amount of blood is accumulated, there is a convenient method of removing the tube and sealing the tube end in one continuous motion.

On thick skinned, calloused fingers with deep grooves it is sometimes difficult to obtain a good seal of the tube to the finger even with an aggressive adhesive. Since the attendant always cleans the skin with alcohol in the area to be lanced, before lancing, adhesion is promoted by using a highly diluted solution of adhesive with alcohol for cleaning. The thin film of adhesive residue which remains after the alcohol evaporates from the skin seals grooves and cracks of the rough skin and provides an adhesive base for the adhesive patch on the tube to adhere to.

Approximately ten percent of patients will not flow enough blood with a single puncture. Therefore, the present invention provides a string of approximately one foot in length for the purpose of compressing the finger on the adjacent joint, which squeezes blood out of the lanced hole. This method is effective enough to obtain one drop of blood out of a smaller than normal size puncture and as much as one cubic centimeter out of a normal puncture.

In the simplest configuration, the outer sleeve and pull tab are eliminated. A tube shaped pouch has an adhesive coating on one end with a latex cover for sealing the lance puncture, and is applied onto the finger for collecting blood.

Other design details illustrated, along with various methods of usage have refinements which progressively improve the desired features of this invention.

BRIEF DESCRIPTION OF THE DRAWINGS

FIGS. 14 and 15 illustrate a plan view and a cross-sectional view of another embodiment of the present invention;

FIG. 16 is an illustration explaining one aspect of the present invention;

DESCRIPTION OF THE PREFERRED EMBODIMENT

Figure 2:
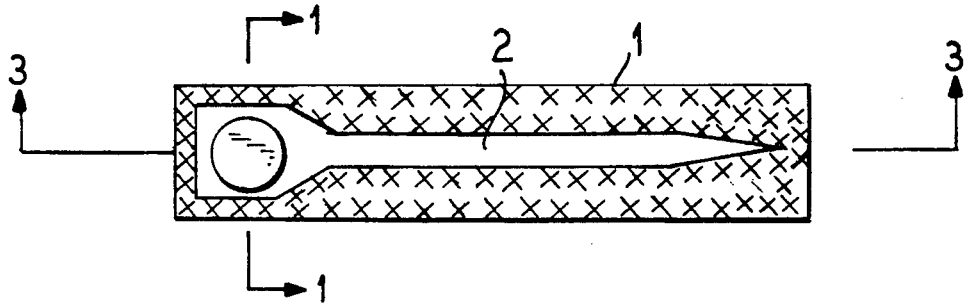
FIGS. 1, 2 and 3 are an end view, plan view, and cross-sectional view of a preferred embodiment of the present invention, in its simplest configuration.
Figure 1:

FIGS. 1 and 2 are respectively an end view and a plan view of this invention in the simplest configuration. A tubular pouch 1 is laminated out of two strips of thin plastic, sealed on the outer periphery to form an inner chamber 2. The chamber is wide on one end then tapers down to a narrow tube with a tapered and closed pointed end.

Figure 3:
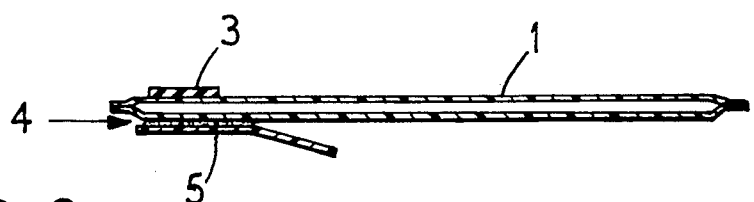

FIG. 3 is a section view of this appliance which illustrates the round latex disk 3 cemented to the top surface of the pouch 1. The opposite surface is coated with an adhesive 4 which is covered with a protective release sheet 5. In use, the release sheet 5 is removed, exposing the adhesive surface, which is placed on the patient's skin, then a puncture is made through the latex disk 3 into the skin. The latex material seals the puncture in the disk, allowing the blood to flow into the tube 1. The tube may be removed by pealing it away from the adhesive and, if necessary, may be replaced by a sterile pad or the like, which adheres to the adhesive.

Figure 4:
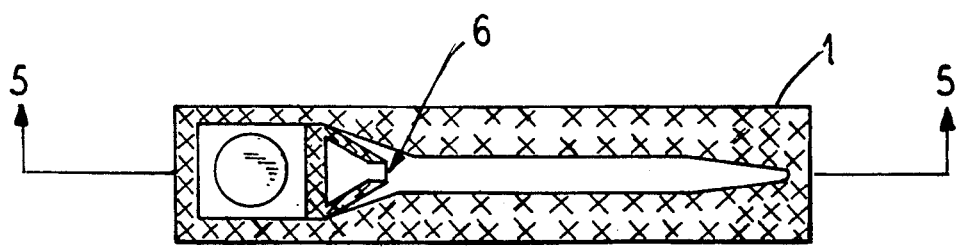
FIG. 4 is a plan view of a modified embodiment of the present invention, with a check valve added.
Figure 5:
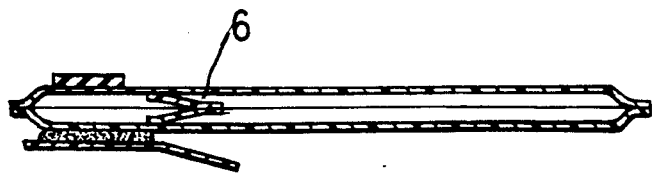
FIG. 5 is a cross-sectional view of the apparatus of FIG. 4.

In FIGS. 4 and 5, a check valve 6 has been added, consisting of two flaps of plastic material at a location adjacent the disk 3. The check valve permits blood to flow into the main part of the tube 1, but prevents its escape.

Figure 6:
FIGS. 6, 7 and 8 are an end view, plan view, and a cross-sectional view of another embodiment of the present invention.
Figure 7:
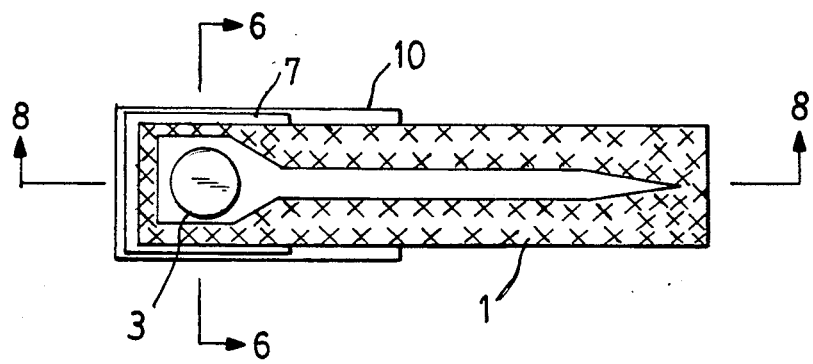
Figure 8:
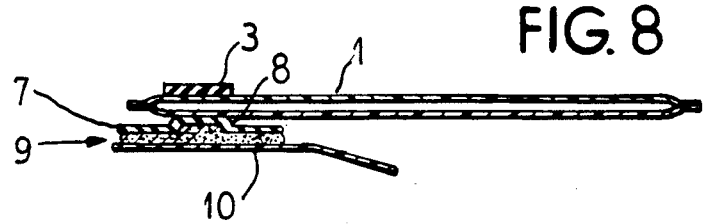

The embodiment shown in FIGS. 6-8 illustrates the pouch assembled with an adhesive patch which provides a substantially better seal between the tube and finger. A rectangular patch 7 formed of latex is attached to the tube 1 within a small area 8 directly opposite the latex disk 3. The opposite surface of the patch is coated with an adhesive 9 then covered with a release sheet 10. The patch material is made of a thin sheet of latex or very pliable plastic sheet such as 0.001 inch thick Saran or the like. The seal is better because the latex can follow the stretch of the skin when the finger is massaged to squeeze out the blood.

Figure 9:
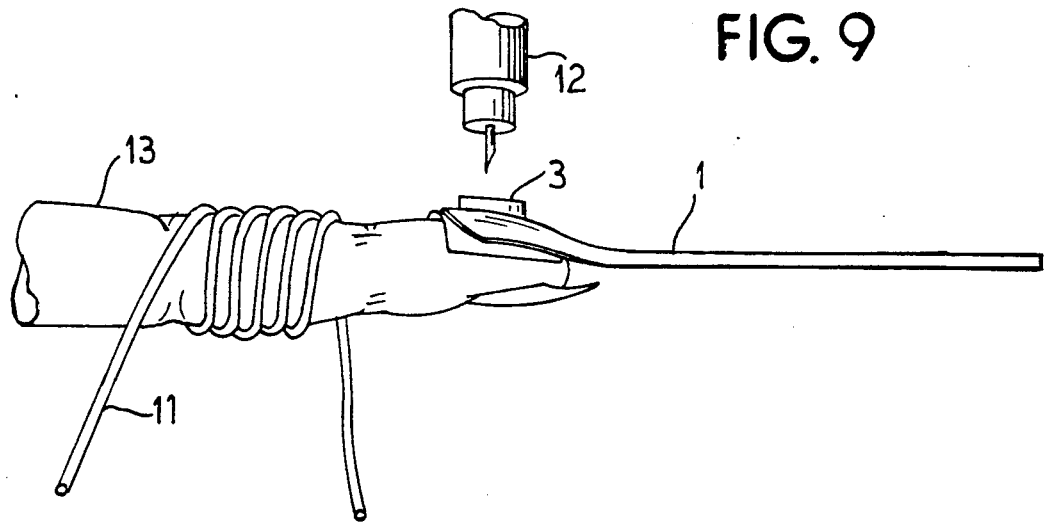
FIG. 9 is an illustration illustrating the use of the present invention.

FIG. 9 illustrates how a finger 13 is wrapped with a short length of string 11 to obtain the desired amount of blood to flow into the tube 1. Also shown is the tube of FIG. 7 as it is applied on the finger tip. A lance 12 is used to pierce through the entire assembly and into the finger. The lance location must always be through the latex disk.

Figure 10:
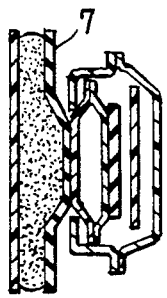
FIGS. 10, 11 and 12 are an end view, plan view, and cross-sectional view, of a further embodiment of the present invention.
Figure 11:
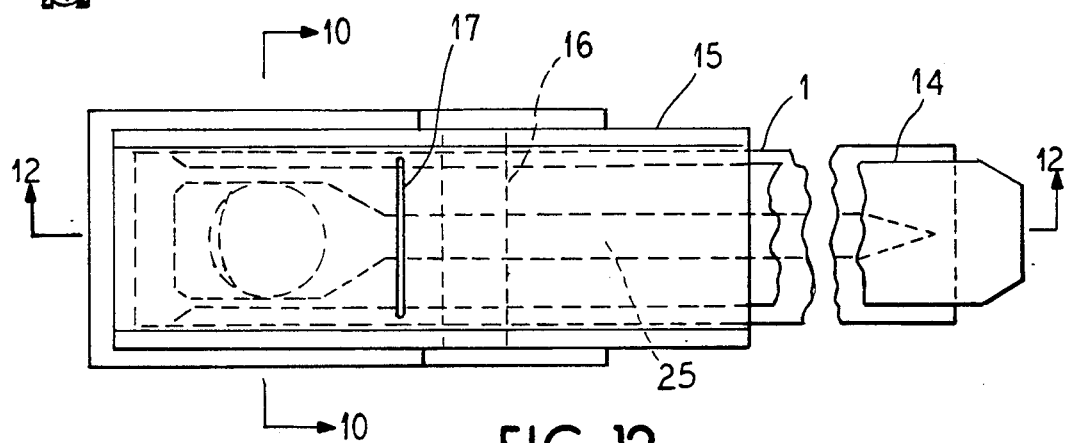

FIGS. 10 and 11 illustrate the tube assembled with a pull tab 14 and a sleeve 15, both formed of thin plastic sheets. The sleeve 15 contains a cross strip 16 made of a thin rigid plastic positioned between the pull tab 14 and the tube 1. A cross slit 17 is cut through the top and bottom surfaces of the sleeve 15.

Figure 13:
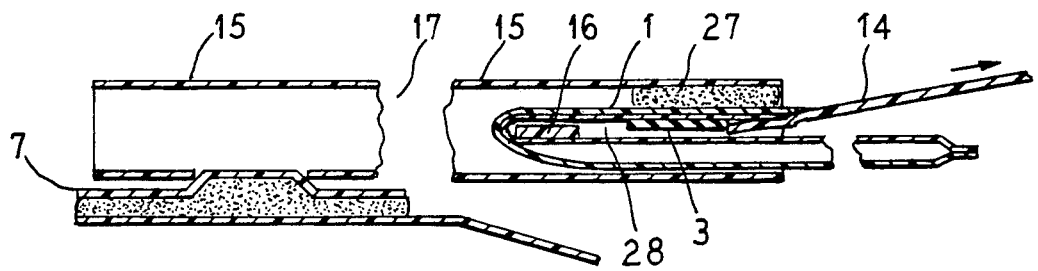
FIG. 13 is cross-sectional view of the embodiment of FIGS. 10-12 during use.

FIG. 13 illustrates the relative positions of the tube 1, latex disk 3 and the sleeve 15 broken, away at the slit 17, when the tab 14 is pulled out.

FIG. 14 illustrates a tube having reagent chambers 18 and 19, a large air surge chamber 20, an air/blood filter 21 and a vent 22. The chambers 18 and 19 preferably contain reagents which react with the blood admitted into the tube 1 by changing color to indicate the amount of blood sugar present, etc.

FIG. 16 illustrates an enlarged view of the latex disk 3 with diametrical compression as shown by arrows 23. The latex disk 3 contains a beveled edge 24. The compression is effected when the disk 3 is assembled, so that it can function to better seal the lance puncture.

Figure 17:
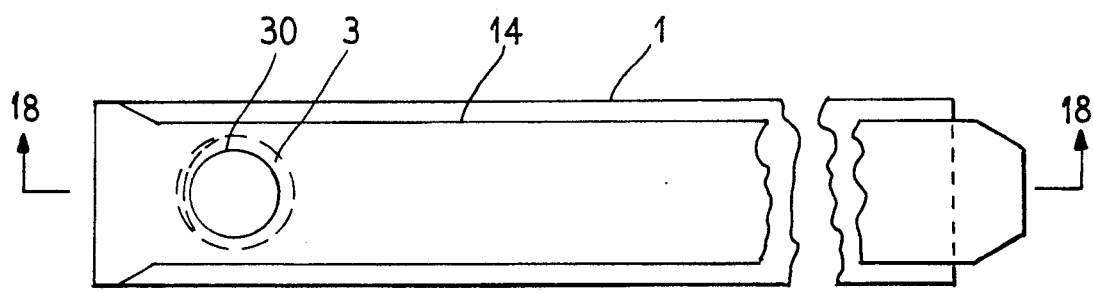
FIGS. 17 and 18 are a plan view and a cross-sectional view of a further embodiment of the present invention.
Figure 18:
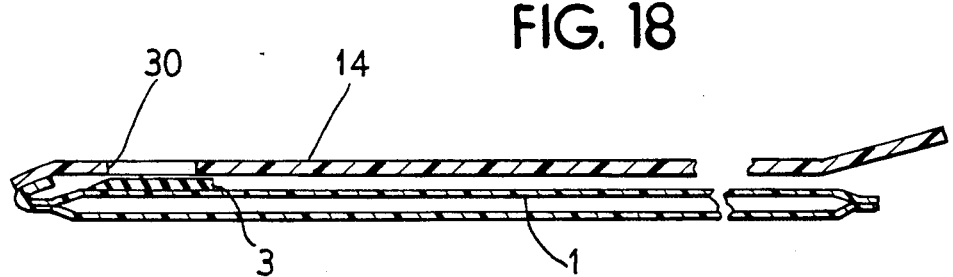

FIG. 17 illustrates a plan view of the tube 1, latex disk 3, and pull tab 14. The pull tab 14 of this design is thicker than in the other embodiments and contains a hole 30 that is positioned directly over the latex disk 3. The hole 30, which overlies the only area that is suitable for lancing, facilitates lancing by minimizing the thickness of the material the lance must puncture.

Figure 19:
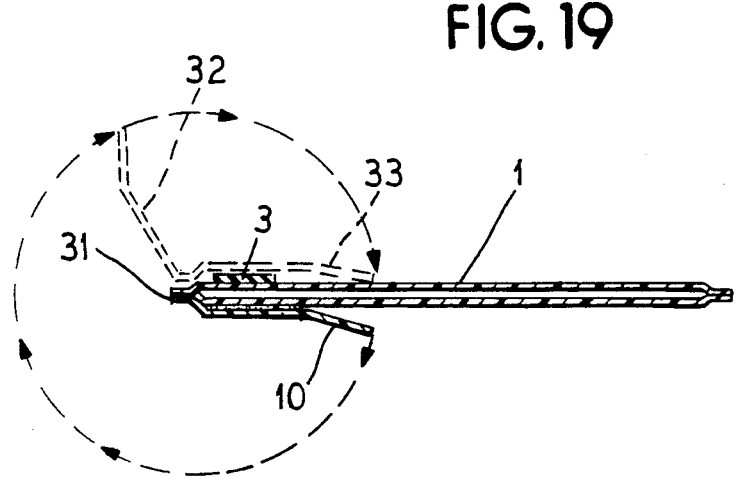
FIG. 19 is a cross-sectional view of an embodiment incorporating a release sheet.

FIG. 19 illustrates the adhesive release sheet 10 attached to the tube end 1. In use, this sheet 10 is flipped over as indicated in dashed lines at position 32. After lancing the finger, the sheet 10 is pressed down over the latex disk 3 into position indicated by dashed lines 33 to press the blood to the right side end of the tube 1. By covering the lanced hole on the disk 3, any possibility of contamination due to leakage is eliminated.

FIG. 14 shows how a narrow tube is formed by laminating two thin sheets of plastic around the periphery. Various chambers and items such as reagents can be inserted within the pouch formed by this method. Illustrated are two types of reagents 18 and 19, a narrow connecting passageway 25, a surge chamber 20 and an air release filter 21.

In use, the blood obtained through a lanced puncture is usually a small quantity of a half or one drop, therefore the tube 1 is designed to minimize spaces where the blood can accumulate and be wasted. For this reason, the connecting passageways 25 are narrowed down to a minimum size which makes it easy to cleanly squeeze the blood through and also contains a minimum wetted area.

The drop of blood which flows into the tube 1 is squeezed through the narrow passageway 25. Any air trapped within the tube is pushed ahead of the blood. The large surge chamber 20 is provided for this air and for any excess blood. The pressure of the surge chamber avoids any substantial back pressure.

For most applications the filter 21 and vent 22 are not required and the tube would be sealed at this end. However, the vent also avoids a high back pressure when used.

If the tube is designed and used for collecting a large volume of blood, the large volume of air within the tube can be more conveniently bled out through a "TEFLON" fiber filter 21 which will pass air but not liquids such as blood. The filter comprises plural fibers trapped in a chamber, which restricts the passage of blood because of the small size of the passageways and the fact that the "TEFLON" is not wetted by the blood.

A small percentage of patients will not bleed out a drop of blood through a single, standard lanced puncture. The finger of these patients can be spirally wrapped with a short length of string 11 as shown in FIG. 9, to squeeze out a drop. This method is efficient enough to obtain as much as one cubic centimeter of blood through a normal lanced puncture.

FIG. 10 illustrates an adhesive patch 7 which is applied on to the finger. After the patient is lanced, the drop of blood is obtained by pressing and squeezing the finger tip. This stretches the skin which causes the adhesive patch 7 to peel off of the finger tip. By constructing the adhesive patch out of a flexible, stretchable material such as latex or a thin "SARAN" plastic material and bonding this adhesive patch 7 to the tube 1, only in the middle, the edges of the patch are free to flex and stretch together with the skin, which retains a good seal.

Some patients have rough, grooved finger tips which are difficult to seal a tube to, even with an aggressive adhesive. A thin coating of adhesive applied onto the finger fills the cracks and grooves and provides an adhesive base for the patch to adhere to. Experiments indicate that this coating may be so thin as to be virtually undetectable and still be effective. Since the technician always cleans the lance area with alcohol before lancing, a diluted adhesive with alcohol can be used for cleaning either routinely or in special situations.

The appliance of the present invention is placed on the finger tip, as shown on FIG. 9 and a lance 12 is used to puncture the finger through the tube. The bottom surface of the tube is sealed against the finger and the top surface contains a self sealing material such as latex. Any blood bleeding out of the finger flows directly into the tube. It is desired to have the latex disk 3 as thin as possible, consistent with providing a good seal. Experiments indicate that a latex disk that is radially compressed, as illustrated in FIG. 16, when bonded to the top surface of the sleeve 1, will provide a better seal of the lanced hole. The latex disk has a coating of pressure sensitive adhesive on its bottom and is preferably formed into a convex shape when adhered to the tube 1, so that the peripheral edge of the disk first adheres to the tube. As the rest of the disk is pushed into contact with the tube, the disk develops a radial compression, which promotes sealing of the puncture. In place of the pressure sensitive adhesive, another bonding method may be used, with the same effect.

Figure 12:
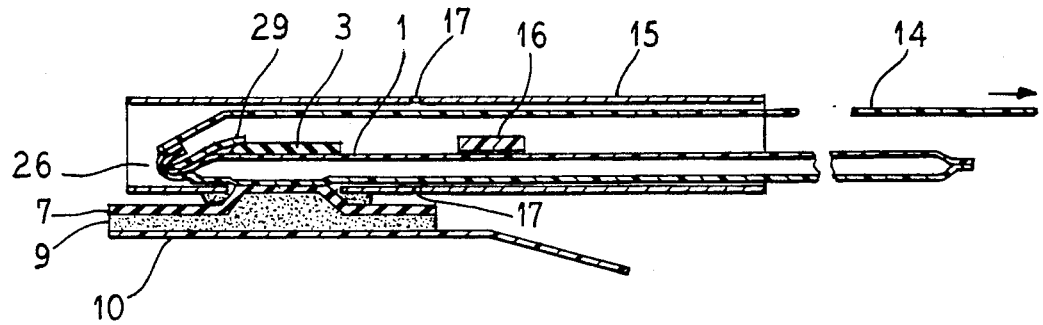

FIG. 10, 11, and 12 shows an appliance which is applied onto the finger tip as shown in FIG. 9. In addition to the design details of the embodiment of FIGS. 6, 7 and 8, this design contains a cover sleeve 15, pull tab 14, cross strip 16 and a break away slit 17.

The procedure for use is as follows:

A—Clean finger with alcohol. Use adhesive/alcohol if necessary.
B—Remove adhesive cover strip 10.
C—Apply adhesive patch 7 onto finger. Position the latex disk 3 directly over the lancing spot.
D—Press the sleeve 15 firmly and vigorously over the adhesive patch 7 to insure a good seal.
E—Lance finger through the sleeve 15 within the area provided by the latex disk 3.
F—Squeeze the finger tip to extract a drop of blood. Use a string wrap if necessary.
G—Press lightly over the disk 3 and pull out the tab 14 until the sleeve 15 breaks off at the slit 17.
H—Write all pertinent information such as date, time, patient's name, room number etc on the top surface of the tab 14.
I—Leave the remaining part of the sleeve 15 with the adhesive patch 7 on the patient's finger.

Referring to FIG. 12, the blood from the finger passes through the adhesive patch 7 and the bottom surface of the tube 1. The blood accumulates in the cavity under the latex disk 3. When the sleeve 15 is lightly pressed and the tab 14 is pulled out as described in "G" above, the sharp crease 26 shown in FIG. 12 rolls to the right and cleanly squeezes the blood through the narrow passage 25 of FIG. 11. The rolling crease 26 is so effective that all traces of blood can be wrung out of this area.

Pulling the tab 14 further out places the crease 26 up against the cross strip 16, which acts as a stop. This stops the pull tab 14 and permanently seals the tube 1. Various methods can be used to retain the tube 1 in this sealed position; for example:

A—The various components can be dimensioned to eliminate the space 28 of FIG. 13. This will create a locking action between the disk 3 and cross strip 16.
B—In the arrangement of FIGS. 11 and 12, the width of the tube 1 can be dimensioned to be a slight interference to the width of the inside of the sleeve 15. Thus, there is no tendency for the parts to slip after the pull tab 14 is pulled.
C—In the arrangement of FIG. 13, a small amount of adhesive 27 may be applied to the inside of the sleeve 15 which bonds to the residual adhesive remaining on the tube 1 from the adhesive used to bond the tube 1 to the adhesive patch 7.

In the arrangement of FIG. 13, the tab 14 is pulled out with enough pressure to break the sleeve 15 at the cross slit 17. The tube 1 containing the blood specimen and sealed at both ends is then detached from the finger. The remaining part of the sleeve 15, together with the adhesive patch 7 is left on the finger, which avoids the need for a band aid and eliminates the need to clean the finger. This further reduces the risk of infection.

The top surface of the tab 14 of FIG. 13 is treated by conventional means for writing pertinent information by means of pencil, ball point pen, etc.

In the arrangement of FIG. 12, when the tab is pulled, the latex disk 3 creases and doubles back on itself along with the tube 1. The leading edge of this disk 3 must be tapered or covered with a plastic film as shown at 29. The tapered edge makes the bending over of the disk easier, and the film 29 also promotes the bending over of the disk. If the edge is left square and sharp, the crease snags and stops at the sharp edge. FIG. 14, 15 and 16 illustrate the bevel 24.

FIG. 17 illustrates a pull tab 14 with a hole 30 positioned directly over the latex disk 3. It is desirable to construct the pull tab 14 out of a rigid material to provide a suitable writing surface. A thick plastic would be difficult to lance through, therefore a clearance hole 30 is provided to eliminate the need to puncture through this item. The pull tab 14 may be constructed out of material thick enough to prevent a lance from penetrating the tube 1 in any area other than through the latex disk 3.

Figure 20:
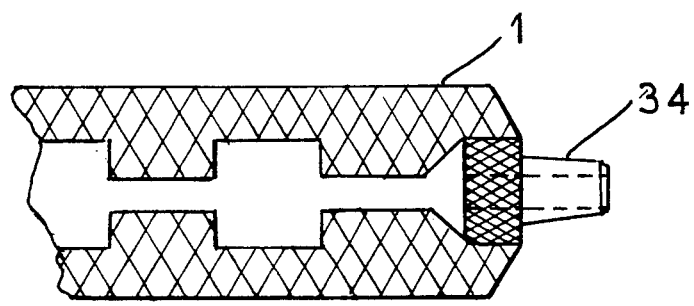
FIGS. 20 and 21 are a cross-sectional view and an end view of a further embodiment of the present invention.
Figure 21:

FIGS. 20 and 21 show an apparatus for collecting a large volume of blood, when necessary. A tube end 41 has a tapered coupling 34, by which another appliance may be connected to the tube, such as a larger container, a tube, a compartment with a quantity of reagent, or the like. FIG. 21 shows an end view of the apparatus of FIG. 20, illustrating the end of the coupling 34.

It will be apparent that various modifications and/or additions may be made in the apparatus of the invention without departing from the essential feature of novelty involved, which are intended to be defined and secured by the appended claims.

WHAT IS CLAIMED IS:

1. A disposable, nonreusable plastic blood collector for collecting a small sample of blood, comprising:
   a means to attach a tube to a person's finger with adhesive and
   means to seal an outside surface of the tube after a lanced puncture is made through said tube.

2. The blood collector according to claim 1, wherein said tube is constructed of thin flexible plastic sheet material.

3. The blood collector according to claim 2, wherein said tube consists of a plurality of narrow passageways and chambers, one of said chambers adapted to store reagents.

4. The blood collector according to claim 2, wherein said tube is attached to a pull tab which axially overlies the tube.

5. The blood collector according to claim 4 wherein said pull tab contains a hole which is positioned over the location of said lanced puncture.

6. The blood collector according to claim 2, wherein said tube includes a fitting at one end thereof, whereby an accessory may be attached to said tube.

7. The blood collector according to claim 1, wherein said adhesive is a thin flexible adhesive sheet with the tube firmly attached only in a small area in the middle of the said adhesive sheet.

8. The blood collector according to claim 7, wherein said tube is constructed of thin flexible plastic sheet material.

9. The blood collector according to claim 8, wherein said tube is attached to a pull tab that axially overlies the tube, and said pull tab is contained within a plastic sleeve with said adhesive sheet positioned external to the sleeve.

10. The blood collector according to claim 9 wherein said sleeve includes a strip of plastic positioned perpendicular to the axis of the sleeve for the purpose of acting as a stop and sealer of the tube when the pull tab is pulled out.

11. The blood collector according to claim 10 wherein said sleeve contains a cross slit for the purpose of breaking the sleeve off at said cross-section.

12. The blood collector according to claim 10 wherein said sleeve and tube comprises of means to maintain a sealed condition of the tube within the sleeve after the tab is pulled out.

13. The blood collector according to claim 1, wherein said means to seal the outside surface of the tube after a lanced puncture is done consists of a thin sheet of pliable sealing material which is radially precompressed when bonded to the tube.

14. A method of collecting blood from a person's finger comprising the steps of applying a flexible tube to a finger, puncturing the finger through said tube, and sealing the outside surface of said tube after said puncturing.

15. The method according to claim 14, including the step of cleaning said finger with a diluted adhesive compound.

16. The method according to claim 14, including the step of winding a string about each finger for the purpose of extruding the desired amount of blood.

* * * * *